(12) United States Patent
Van Der Pluijm et al.

(10) Patent No.: US 11,931,696 B2
(45) Date of Patent: Mar. 19, 2024

(54) GAS SEPARATION ELEMENTS AND MODULES

(71) Applicants:Fujifilm Manufacturing Europe B.V., Tilburg (NL); Fujifilm Corporation, Tokyo (JP)

(72) Inventors: Anton Van Der Pluijm, Tilburg (NL); Petrus Henricus Maria Van Kessel, Tilburg (NL); Shigehide Itoh, Tilburg (NL); Yujiro Itami, Tilburg (NL); Davide Bocciardo, Tilburg (NL)

(73) Assignees: Fujifilm Manufacturing Europe B.V., Tilburg (NL); Fujifilm Corporation, Tokyo (JP)

( * ) Notice: Subject to any disclaimer, the term of this patent is extended or adjusted under 35 U.S.C. 154(b) by 0 days.

(21) Appl. No.: 17/636,528

(22) PCT Filed: Aug. 28, 2020

(86) PCT No.: PCT/EP2020/074044
§ 371 (c)(1),
(2) Date: Feb. 18, 2022

(87) PCT Pub. No.: WO2021/038020
PCT Pub. Date: Mar. 4, 2021

(65) Prior Publication Data
US 2022/0274066 A1 Sep. 1, 2022

(30) Foreign Application Priority Data
Aug. 30, 2019 (GB) ....................... 1912462

(51) Int. Cl.
*B01D 53/22* (2006.01)
*B01D 63/10* (2006.01)
(Continued)

(52) U.S. Cl.
CPC ......... *B01D 63/103* (2013.01); *B01D 53/228* (2013.01); *B01D 69/10* (2013.01);
(Continued)

(58) Field of Classification Search
CPC .... B01D 69/10; B01D 63/103; B01D 53/228; B01D 2313/146; B01D 2313/143; C07C 7/144
See application file for complete search history.

(56) References Cited

U.S. PATENT DOCUMENTS 4,728,394 A * 3/1988 Shinjou ............... B01D 69/10
162/146
4,795,559 A * 1/1989 Shinjou ............... B01D 69/10
210/490

(Continued)

FOREIGN PATENT DOCUMENTS

EP 2433702 A1 3/2012
WO 2016/049281 A1 3/2016

*Primary Examiner* — Anthony R Shumate
(74) *Attorney, Agent, or Firm* — Banner & Witcoff, Ltd.

(57) ABSTRACT

A gas separation element comprising a membrane sheet and a permeate spacer, wherein the membrane sheet comprises a porous support and a discriminating layer, CHARACTERISED IN THAT:
(a) the permeate spacer has an open space volume of at least 0.0004 m³/m²; and
(b) the membrane sheet has an aspect ratio of at least 1.5.

20 Claims, 2 Drawing Sheets

(51) Int. Cl.
   *B01D 69/10* (2006.01)
   *C07C 7/144* (2006.01)

(52) U.S. Cl.
   CPC ........ *C07C 7/144* (2013.01); *B01D 2313/143* (2013.01); *B01D 2313/146* (2013.01)

(56) References Cited

U.S. PATENT DOCUMENTS

| | | | | |
|---|---|---|---|---|
| 4,814,079 A | * | 3/1989 | Schneider | B01D 63/10 210/321.83 |
| 5,143,614 A | * | 9/1992 | Soria | C04B 41/009 210/450 |
| 5,906,739 A | * | 5/1999 | Osterland | B01D 63/063 210/321.78 |
| 8,404,132 B2 | * | 3/2013 | De Brabander | B81B 3/0021 216/27 |
| 8,496,825 B1 | * | 7/2013 | Jons | B01D 69/02 210/500.21 |
| 2004/0103832 A1 | * | 6/2004 | Gross | F23N 5/006 110/346 |
| 2005/0173333 A1 | * | 8/2005 | Kloos | B01D 63/082 210/488 |
| 2006/0000777 A1 | * | 1/2006 | Da Costa | B01D 71/32 210/651 |
| 2007/0068864 A1 | * | 3/2007 | Cruz | B01D 63/103 210/321.74 |
| 2008/0193734 A1 | * | 8/2008 | Whitnall | B01J 20/3219 428/221 |
| 2010/0024651 A1 | * | 2/2010 | Bansal | B01D 53/229 96/13 |
| 2010/0051535 A1 | * | 3/2010 | Hokazono | B01D 71/36 264/413 |
| 2010/0140161 A1 | * | 6/2010 | Haynes | B01D 63/103 156/227 |
| 2010/0300545 A1 | * | 12/2010 | Biaggi | B63B 27/24 137/234.6 |
| 2011/0030559 A1 | | 2/2011 | Itami | |
| 2011/0042301 A1 | * | 2/2011 | Zhang | B01D 71/02 210/500.21 |
| 2012/0219756 A1 | * | 8/2012 | Yoshida | B01D 69/10 428/141 |
| 2015/0336056 A1 | | 11/2015 | Ouchi | |
| 2016/0256828 A1 | * | 9/2016 | Van Der Burg | B01D 63/103 |
| 2018/0001276 A1 | * | 1/2018 | Shibata | B01D 67/0046 |
| 2018/0147546 A1 | | 5/2018 | Kodama et al. | |
| 2018/0178166 A1 | * | 6/2018 | Okubo | B01D 69/10 |
| 2019/0247794 A1 | * | 8/2019 | Nishi | B01D 63/103 |
| 2019/0282962 A1 | * | 9/2019 | Konda | B01D 61/025 |
| 2020/0360869 A1 | * | 11/2020 | Frayne | B01D 67/0041 |
| 2020/0376443 A1 | * | 12/2020 | Zheng | C02F 1/44 |
| 2022/0297056 A1 | * | 9/2022 | Van Der Pluijm | B01D 69/10 |
| 2022/0305446 A1 | * | 9/2022 | Bagge | B01D 71/80 |

\* cited by examiner

GAS SEPARATION ELEMENTS AND MODULES

RELATED APPLICATIONS

This application is a National Stage Application under 35 U.S.C. 371 of co-pending PCT application PCT/EP2020/074044 designating the United States and filed Aug. 28, 2020; which claims the benefit of GB application number 1912462.7 and filed Aug. 30, 2019, each of which are hereby incorporated by reference in their entireties.

This invention relates to gas separation elements, to gas separation modules and to their uses.

Gas separation modules typically comprise one or more membrane sheets and a permeate spacer. The membrane sheet is for separating a feed gas mixture into a permeate which has passed through a membrane and into the permeate spacer and a retentate which does not pass through the membrane. The permeate and retentate typically comprise the same gases as the feed gas mixture, but one is enriched in at least one of the gases present in the feed gas and the other is depleted in that same gas. Often the gas separation elements further comprise a feed spacer to provide a pathway between membranes through which feed gas may travel. Feed spacers typically have a relatively large mesh size to accommodate the flow of feed gas. Typically a stack of gas separation elements are wound spirally onto a perforated permeate collection tube such that the feed spacers and permeate spacers are in alternating order and the permeate collection tube collects gas which has permeated through the membrane and into the permeate spacer.

In spiral gas separation modules, the outside edges of the gas separation elements are generally sealed on all but one side, allowing access to the permeate spacer only from a radial direction through the membrane. The gas separation elements are placed with the unsealed edge adjacent to a perforated permeate collection tube and oriented along the length of the tube, allowing the permeate to flow into the permeate collection tube and preventing retentate from entering the tube.

After the gas separation elements are wound onto a permeate collection tube, some type of external restraining means such as a hard shell, straps, anti-telescoping device or a bypass screen, or a combination thereof, may be used to hold the spiral wound gas separation elements in tight formation around the tube. The spiral module is then loaded into a pipe-like housing or pressure vessel which is operated at a pressure drop across the module as the gas being filtered flows through.

The present inventors have found that gas separation elements and modules as defined below are robust and can separate $CO_2$ and higher alkanes ($C_nH_{2n+2}$ with n>1) from $CH_4$ (methane) with high selectivity and at a good flux rate. According to a first aspect of the present invention there is provided a gas separation element comprising a membrane sheet and a permeate spacer, wherein the membrane sheet comprises a porous support and a discriminating layer, CHARACTERISED IN THAT:
 (a) the permeate spacer has an open space volume of at least 0.0004 m³/m²; and
 (b) the membrane sheet has an aspect ratio of at least 1.5.

The gas separation elements ("GSEs") of the present invention are robust, stable in humid environments for long periods of time and have good permeance and selectivity.

In this specification the term "comprising" is to be interpreted as specifying the presence of the stated parts, steps or components, but does not exclude the presence of one or more additional parts, steps or components. The phrase "gas separation element" and "GSE" are used interchangeably in this specification.

BRIEF DESCRIPTION OF THE DRAWINGS

In the accompanying drawings:

In FIG. 1, the GSE comprises the lower part of a first gas separation membrane (18a), the upper part of a second gas separation membrane (18b), a permeate spacer (24) provided between these gas separation membranes and an optional feed spacer (16).

FIG. 2 is analogous to FIG. 1 except that instead of single macroporous sheet there are three macroporous sheets as permeate spacer (24) placed in between the lower part of a first gas separation membrane (18a) and the upper part of a second gas separation membrane (18b). The cumulative open space volume of the three macroporous sheets is at least 0.0004 m³/m².

Referring to FIG. 3, a membrane stack and module according to the present invention may be prepared as follows: a permeate spacer (24) is attached to permeate collection tube (12) having perforations (14). A stack of alternate membrane envelopes (26) and permeate spacers (24) are aligned on the permeate collection tube (12). The membrane envelopes (26) comprise a rectangular membrane sheet (18) folded around an optional feed spacer (16) and the folded edge of the membrane envelope (26) abuts the permeate collection tube (12). The stack is then wound around the permeate collection tube (12) to provide a membrane structure comprising two parallel end faces and a third face of circular cross-section. Adjacent membrane envelopes (26) are adhered together such that feed gas passing from the left to the right in FIG. 3 can pass along the feed spacer (16) but cannot enter the permeate spacer (24) without first passing through the walls of membrane sheets (18). In a preferred embodiment (not shown), in place of each permeate spacer (24) there is used a permeate spacer comprising at least 3 macroporous sheets. Feed gas may be prevented from entering the permeate spacer (24) without first passing through the membranes (18) by depositing adhesive (sometimes called a "glue line") along the left and right outside edges of the membrane envelopes (26), thereby forming a gas-tight seal.

Referring to FIG. 4, a spiral wound gas filtration module according to the present invention is designated generally by the numeral (10). The module has a central permeate collection tube (12) having perforations (14) along its length. Membrane envelope (26) is wound about the permeate collection tube (12). Each membrane envelope is oriented to present an edge generally adjacent the tube (12) a pair of side edges and an axial edge distal from the tube and oriented to be in parallel with the axis of the tube. A liquid adhesive (36) is provided along two of the outer sides of each the membrane envelope (26) in order to provide an inlet for the feed flow and to provide a gas-tight seal between tube and membrane envelope to avoid flow entering the collection tube (12). The third and fourth side of each membrane envelope (26) is open (i.e. no liquid adhesive is applied) for feed flow inlet and out let. Permeate spacers (24), membrane sheets (18) and feed spacers (16) are thus spirally wound around permeate collection tube (12) with permeate spacer (24) located adjacent tube (12) and in gas communication therewith. Referring to the series of layers of membrane sheet (18) and a second membrane sheet (18), feed spacer (16) as a membrane envelope (26), typically a stack of membrane envelopes (26) are spirally wound about permeate tube (12) with a permeate spacer (24) located between adjacent membrane envelope (26). During preparation of the modules, the adhesive (36) is applied to the permeate spacer and connected to each membrane envelope at three sides (with only the side open to the collection tube for permeate providing communication to the collection tube) and may be partially cured before the various layers are wound onto the permeate collection tube (12) and then heated after winding to further cure the adhesive (36).

The aspect ratio of the GSE allows the GSE to be wound spirally onto a perforated tube (12) lengthwise to provide a gas separation module having a large surface are for separating and/or purifying gases.

The module may optionally be formed without feed spacers (16).

Figure 1:
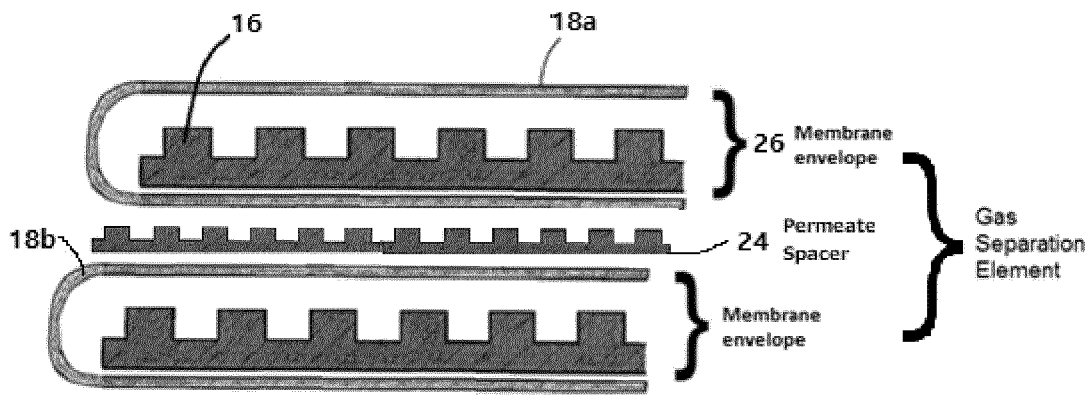
FIG. 1 is a schematic vertical sectional view of a GSE according to the present invention comprising two membrane sheets, a permeate spacer and optional feed spacer.
Figure 2:
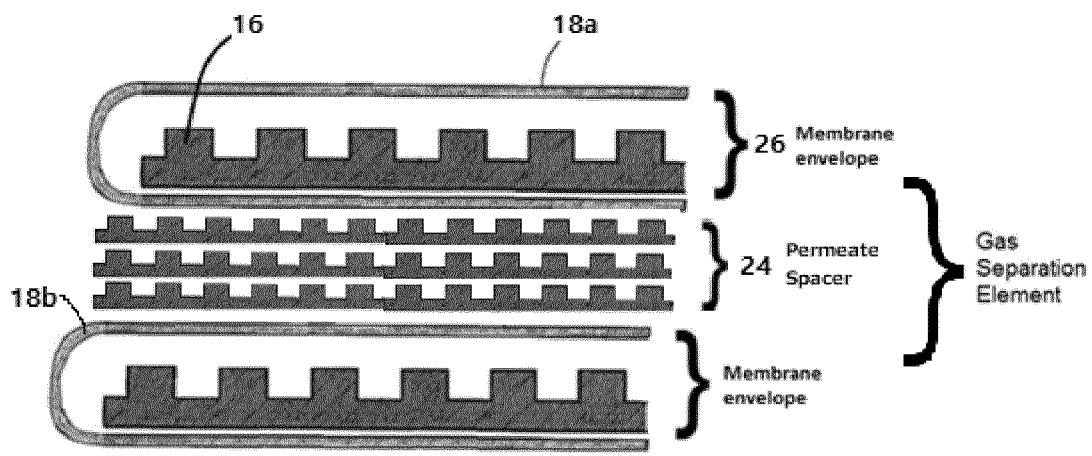
FIG. 2 is a side view of a GSE according to the present invention comprising two membrane sheets and a permeate spacer comprising 3 macroporous sheets, wherein each of the two membranes sheets is part of a separate membrane envelope.
Figure 3:
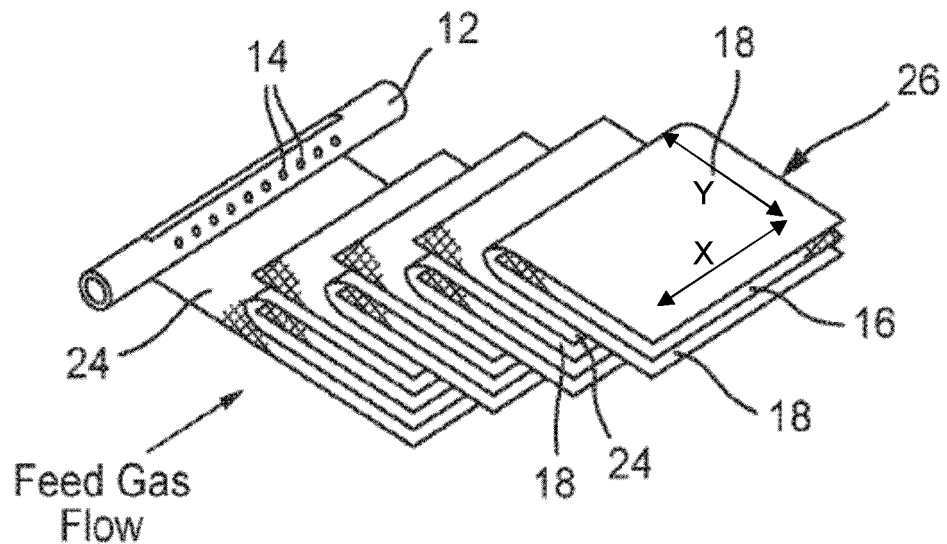
FIG. 3 illustrates how a membrane stack and module according to the present invention may be prepared.

Furthermore, FIG. 3 illustrates the width dimension (X) and the length direction (Y) of the folded membrane (18), permeate spacer (24) and feed spacer (16).

The membrane sheet (18) preferably has an aspect ratio of at least 1.5, e.g. a width (X) which is at least 1.5 times (especially 1.75 to 2.5 times) its length (Y). The membrane sheet (18) preferably has a width (X) of 0.65 to 0.85 m. The membrane sheet preferably has a length (Y) of 0.35 to 0.53 m.

The membrane sheet (18) preferably has a n-$C_4H_{10}$ gas permeance of 30 to 800 GPU, more preferably 100 to 750 GPU and especially 150 to 700 GPU. The n-$C_4H_{10}$ gas permeance of the membrane may be measured using a patch test (e.g. by the method described in the Examples section below).

The discriminating layer is preferably a polymer which provides the membrane sheet with has a n-$C_4H_{10}$ gas permeance of 30 to 800 GPU. Preferably the discriminating layer has an average thickness of at least 0.6 µm to 3.6 µm, more preferably 0.8 µm to 3.0 µm and especially 1.2 µm to 2.4 µm.

Preferably from 5 to 20% of the thickness of the discriminating layer is present within the porous support. One may determine the % of the thickness of the discriminating layer which is present within the porous support by cutting through the support and examining a side view of the support using a scanning electron microscope ("SEM"). Then by measuring the average thickness of the part of the discriminating layer which is present within the porous support and dividing this by the average of the total thickness of the discriminating layer and multiplying by 100% one finds the % of the thickness of the discriminating layer which is present within the porous support. Similarly one may determine the average thickness of the discriminating layer using a SEM.

The function of the discriminating layer is to preferentially discriminate between gases, separating a feed gas mixture into a permeate which passes through the membrane and a retentate which does not pass through the membrane. The permeate and retentate typically comprise the same gases as the feed gas mixture, but one is enriched in at least one of the gases present in the feed gas and the other is depleted in that same gas.

Preferably the discriminating layer comprises a polysiloxane, especially a cross-linked polysiloxane, for example as described for the gutter layer in U.S. Pat. No. 5,286,280.

Preferably the polysiloxane is or comprises a polydimethylsiloxane (PDMS), especially a smooth PDMS coating. One may form a smooth PDMS coating by applying a PDMS (especially a PDMS having high gas permeability) onto a porous support. However, as PDMS has a low surface free energy, PDMS readily infiltrates the pores of a porous support and this can cause defects in the resultant membrane sheet. On the other hand, if PDMS is applied to porous support as a very thick layer to prevent such defects, or if phenyl-modified PDMS is used to improve the surface free energy of PDMS, the gas permeability of the resultant membrane sheet may deteriorate. In order to overcome the defects related to this coating, the polysiloxane is preferably as defined in US20180147546, claim 1. Thus in a preferred embodiment the polysiloxane is preferably obtained from a process comprising applying a composition comprising (a) and (b) to a porous support to form a coating film thereon and curing the coating film to form the polysiloxane discriminating layer, wherein (a) is a crosslinkable polysiloxane compound that has a structural unit represented by formula (a1) below, a structural unit represented by formula (a2) below, and at least one structural unit selected from the group consisting of a structural unit represented by formula (a3) below and a structural unit represented by formula (a4) below and that does not have a hydrosilyl group, and (b) is a crosslinkable polysiloxane compound that has a structural unit represented by formula (b1) below, a structural unit represented by formula (b2) below, and at least one structural unit selected from the group consisting of a structural unit represented by formula (b3) below and a structural unit represented by formula (b4) below and that does not have a vinyl group,

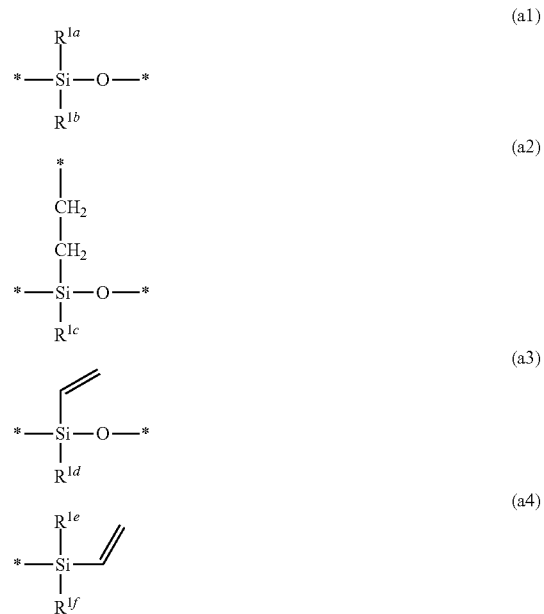

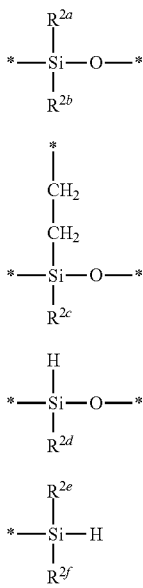

wherein:
R$^{1a}$ to R$^{1f}$ and R$^{2a}$ to R$^{2f}$ each independently represent a substituent that is not reactive with a vinyl group or a hydrosilyl group; and
* represents a linking site, where a linking site * in *—Si— and —O—* is a linking site in a siloxane bond and a linking site * in —CH—CH$_2$—* is a linking site with a Si atom constituting a siloxane bond.

In another embodiment the polysiloxane has been obtained from curing a composition comprising a partially crosslinked polysiloxane and an alkoxy titanium compound. This embodiment is preferred because the resultant polysiloxane discriminating layer is very smooth and advantageously often permeates into the porous support to only a small extent, providing a discriminating layer having good gas separation properties.

When the curing is photocuring, the composition preferably further comprises a photoinitiator. Photoinitiators are widely available commercially and include, for example, 4-isopropyl-4'-methyldiphenyliodonium tetrakis(pentafluorophenyl) borate (C$_{40}$H$_{18}$BF$_{20}$I) from TCI.

Preferably the membrane sheets are capable of discriminating between higher alkanes and methane.

The porous support may be, for example, a microporous organic or inorganic membrane, or a woven or non-woven fabric. The support may be constructed from any suitable material. Examples of such materials include polysulfones, polyethersulfones, polyimides, polyetherimides, polyamides, polyamideimides, polyacrylonitrile, polycarbonates, polyesters, polyacrylates, cellulose acetate, polyethylene, polypropylene, polyvinylidenefluoride, polytetrafluoroethylene, poly(4-methyl 1-pentene) and especially polyacrylonitrile ("PAN").

The porous support preferably comprises less than 7 mg/m$^2$ of monovalent metal ions, more preferably less than less than 5 mg/m$^2$ of monovalent metal ions. In one embodiment the porous support is free from or essentially free monovalent metal salt ions, e.g. no monovalent metal ions can be detected in the porous support. In another embodiment the porous support comprises at least 0.5 mg/m$^2$ of free monovalent metal salt ions.

Porous supports comprising less than the above-stated amounts of monovalent metal ions may be prepared in the laboratory using raw materials that have a low content of monovalent metal ions. Alternatively, while many porous supports available commercially have a monovalent metal ion content of more than 10 mg/m$^2$ (especially porous supports from GMT GmbH), porous supports comprising less than the above-stated amounts of monovalent metal ions may be obtained from MICRODYN-NADIR. Examples of commercially available porous supports comprising less than 10 mg/m$^2$ of monovalent metal ions include UA100T from MICRODYN-NADIR.

Surprisingly the gas separation elements and modules according to the present invention which comprise a porous support comprising less than 10 mg/m$^2$ of monovalent metal ions have good robustness and selectivity compared to gas separation elements and modules which comprise a porous support comprising higher levels of monovalent metal ions. While not wishing to be bound by any particular theory, possibly the higher concentration of monovalent metal ions used in the porous support of prior membranes adversely affects the cross-linking ability of the siloxanes used to form the polysiloxane discriminating layer on such porous supports and this in turn reduces the robustness of the resultant GSE and module which contain the membranes. The GSEs and modules of the present invention are particularly useful for separating higher alkanes (C$_n$H$_{2n+2}$ wherein n is >1) from methane (CH$_4$).

The porous support preferably comprises less than the abovementioned amounts of the following monovalent metal ions: Na$^+$, K$^+$, Li$^+$, Cs$^+$ and Li$^+$.

The amount of monovalent metal ions present in the porous support may be determined by the extracting the monovalent metal ions from the porous support and calculating the weight of the monovalent metal ions in mg per m$^2$ of porous support. For example, one may dissolve a sample of a porous support of known area in acid with heating and then measure the amount monovalent metal ions in the resultant solution in mg and divide this by the area of the porous support in m$^2$.

In one embodiment, the area of the membrane sheet and permeate spacer are identical, for example the length (Y) and width (X) of the membrane sheet and permeate are identical. In another embodiment, the area of the membrane sheet and permeate spacer are not identical, for example when the length (Y) of the permeate spacer is longer than the length (Y) of the membrane sheets.

Optionally the porous support has been subjected to a corona discharge treatment, glow discharge treatment, flame treatment, ultraviolet light irradiation treatment or the like, e.g. for the purpose of improving its wettability and/or adhesiveness.

The porous PAN support may consist entirely of polyacrylonitrile or it may comprise polyacrylonitrile and a further component, e.g. the PAN support is optionally a non-woven support made of something other than polyacrylonitrile which is coated with polyacrylonitrile. As an example of a non-woven support made of something other than polyacrylonitrile there may be used any polymer support (other than polyacrylonitrile) having a thickness, for example, in the range of 50 to 300 μm, preferably 75 to 250 μm. However a preferred non-woven support made of something other than polyacrylonitrile is a polyethyleneterephthalate (PET) support having a thickness in the range of 100 to 200 μm.

The porosity at the surface of the porous support may also be expressed as a % porosity, i.e.:

$$\% \text{ porosity} = 100\% \times \frac{\text{(area of the surface which is missing due to pores)}}{\text{(total surface area)}}$$

The areas required for the above calculation may be determined by inspecting the surface of the porous support using a SEM.

Thus, in a preferred embodiment, the porous support has a % porosity >1%, more preferably >3%, especially >10%, more especially >20%.

The porosity of the porous support may also be expressed as a $CO_2$ gas permeance (units are $m^3(STP)/m^2 \cdot s \cdot kPa$). When the composite membrane is intended for use in gas separation the porous support preferably has a $CO_2$ gas permeance of 5 to $150 \times 10^{-5}$ $m^3(STP)/m^2 \cdot s \cdot kPa$, more preferably of 5 to 100, most preferably of 7 to $70 \times 10^{-5}$ $m^3(STP)/m^2 \cdot s \cdot kPa$.

Alternatively the porosity is characterised by measuring the $N_2$ gas flow rate through the porous support. Gas flow rate can be determined by any suitable technique, for example using a Porolux™ 1000 device, available from porometer.com.

Typically the Porolux™ 1000 is set at the maximum pressure (about 34 bar) and one measures the flow rate (L/min) of $N_2$ gas through the porous support under test. The $N_2$ flow rate through the porous support at a pressure of about 34 bar for an effective sample area of 2.69 $cm^2$ (effective diameter of 18.5 mm) is preferably >1 L/min, more preferably >5 L/min, especially >10 L/min, more especially >25 L/min. The higher of these flow rates are preferred because this reduces the likelihood of the gas flux of the resultant composite membrane being reduced by the porous support.

The abovementioned % porosity and permeance refer to the porous support used to make the composite membrane (i.e. before the selective layer and any other layers have been applied thereto).

The pores passing through the porous support preferably have an average diameter of 0.001 to 10 µm, preferably 0.01 to 1 µm (i.e. before the porous support has been converted into a membrane sheet). The pores at the surface of the porous support will typically have a diameter in the range of 0.001 to 0.1 µm, preferably 0.005 to 0.05 µm. The pore diameter may be determined by, for example, viewing the surface of the porous support using aSEM or by cutting through the porous support and measuring the diameter of the pores within the porous support, again by SEM.

The porous support preferably has an average thickness in the range of 20 to 500 µm, more preferably 50 to 400 µm and especially 100 to 300 µm.

Typically the discriminating layer is present on only one side of the porous support or is partially or wholly within the porous support.

Preferably the membrane sheet is prepared by a method comprising coating a porous support comprising less than 10 mg/m² of monovalent metal ions with a composition comprising a curable polysiloxane, an alkoxy titanium compound and optionally an initiator (e.g. a photoinitiator). The partially curable polysiloxane may be further cured when present on the porous support, e.g. by ageing, heating and/or irradiation. This method provides particularly smooth discriminating layers which penetrate the porous support to only a small extent. The abovementioned composition is preferably applied to the porous support at a temperature of 10 to 35° C.

The coating method is not particularly limited and includes spin coating, slot die coating, blade coating, bar coating, screen printing, stencil printing, roll coating, curtain coating, spray coating, dip coating, ink-jet printing, immersion and combinations of two or more of the foregoing. Spin coating, screen printing, dipping and the like are preferable.

Optionally the membrane sheet comprises more than one discriminating layer.

The permeate spacer (24) has an aspect ratio of at least 1.5, e.g. a width (X) which is at least 1.5 times its length (Y). Preferably the permeate spacer (24) has an aspect ratio of at least 1.75, e.g. 1.75 to 2.5. The permeate spacer (24) preferably has a width (X) of 0.65 to 0.85 m. The permeate spacer (24) preferably has a length (Y) of 0.35 to 0.53 m.

Preferably the length and width of the permeate spacer are each respectively 75% to 125%, more preferably 90% to 110%, especially 95% to 105% and more especially 99% to 101% of the length and width respectively of the membrane sheet (18).

The permeate spacer (24) is included to ensure that there is a pathway for gas which has permeated through the membrane (18) to travel to the perforations (14) in the permeate collection tube (12). Preferably the permeate spacer (24) has an open space volume of at least 0.00045 $m^3/m^2$, e.g. an open space volume of 0.00046 to 0.0020 $m^3/m^2$.

The open space volume of the permeate spacer (24) is the total volume of 1 $m^2$ of the permeate spacer (24) which may be occupied by gas. The open space volume of the permeate spacer (24) may be calculated based on the effective area of membrane after correcting the X and Y lengths on glued line dimensions (i.e. deleting the area of the permeate spacer (24) which is glued as that has no open space), thickness, weight per area and density of spacer materials in the permeate space.

When the permeate spacer (24) comprises a single macroporous sheet one may calculate the open space volume ("OSV") of the permeate spacer using the Formula (1) below:

$$OSV = (V1 - (BW/R1)) \quad \text{Formula (1)}$$

wherein:
 OSV is the open space volume of the permeate spacer (24) in $m^3/m^2$ of the permeate spacer;
 V1 is the thickness of the macroporous sheet in metres;
 BW is the weight of 1 $m^2$ of the macroporous sheet; and
 R1 is the density in $g/m^3$ of the material from which the macroporous sheet is constructed.

When the permeate spacer (24) comprises more than one macroporous sheet, the open space volume ("OSV") of the permeate spacer (24) is the sum of the open space volumes $((V1-(BW/R^1))$ for the macroporous sheets making up the permeate spacer (24). Therefore one may use Formula (1) to calculate the OSV for each macroporous sheet present in the permeate spacer (24) and add the OSV for the macroporous sheets together to determine the OSV of the permeate spacer (24) as a whole.

Preferably the permeate spacer (24) has an average thickness of at least 900 µm, preferably an average thickness in the range of 1,000 to 5,000 µm, especially 1,200 to 4,000 µm.

The permeate spacer (24) preferably comprises one or more than one (e.g. 2 to 10, preferably 2 to 6) macroporous sheet. Macroporous sheets typically have a very high gas permeability. The macroporous sheet(s) are not included to discriminate between gases but instead to provide a pathway for the permeate gases to flow through. Suitable macroporous sheets include woven or non-woven fabric, especially a knitted fabric, more especially a warp knitted fabric or a weft knitted fabric. Knitted fabrics typically comprise a plurality of consecutive rows of loops, called stitches. As each row progresses, a new loop is pulled through an existing loop. The active stitches are held on a needle until another loop can be passed through them. This process eventually results in a knitted fabric. Knitting may be done by hand or more typically by machine.

Suitable weft knitted fabrics can be made from one yarn, although more than one yarn can be used to achieve particular patterns and surface profiles in the fabric and create a surface texture which gives rise to the desired contact area. The yarn is typically inserted in a horizontal or weft direction, hence the classification as weft knitted.

Rows of stitches in knitted fabrics are called 'courses' and columns of stitches are called 'wales'.

Warp knitted fabrics are also composed of loops arranged in wales and courses. The yarn is typically inserted in the vertical or warp direction, hence the classification as warp knitted. They require at least one warp yarn to supply each needle on a knitting machine manufacturing the warp knitted fabric. They are normally made with 2 or more sets of warp yarns. Their properties normally lie between those of woven and weft knitted fabrics.

A particularly preferred warp knitted fabric is tricot. In tricot fabrics the yarn typically zigzags vertically along columns of knit resulting in a series of wales (ribs) on one side (the so-called wales side) and on the other (back) side is the course side where the courses are in series parallel to the orientation of the wales. The orientation in the present invention as such is not limited, although it is preferred that the side facing the membrane sheet has a contact surface area therewith of less than 45%.

The permeate spacer (24) optionally has a different surface profile on each side. For example, one side may comprise mostly 'courses' (referred to as the course side) and the other side may comprise mostly 'wales' (referred to as the wales side).

Preferably the permeate spacer (24) has a pickup of 12 to 35 wt %, especially 13 to 30 wt %, as determined by AATCC Test Method 97-2009. This method determines the total content of water, enzymes and matter extractable using organic solvent (e.g. hexane). AATCC is the American Association of Textile Chemists and Colorists.

When the permeate spacer (24) comprises two or more macroporous sheets (e.g. fabrics), the open space volume of permeate spacer (24) is the total open space volume of the macroporous sheets used to make the permeate spacer added together. For example, see Table 5 below where the permeate spacers comprise several macroporous sheets and the open space volume of each permeate spacer (24) is the total open space volume of the macroporous sheets used to make that permeate spacer (24). The macroporous sheets used to make a permeate spacer (24) may be the same as each other or different. For example, where one side of the macroporous sheet is rough and the other relatively smooth, one may orientate two sheets of the macroporous sheet 'back to back' with the relatively smooth faces in contact so that the relatively rough faces contact the membrane sheets and achieve the desired contact area. One may choose macroporous sheets having an uneven surface profile in order to ensure that the desired contact area between the permeate spacer and the membrane(s) is kept below 50%.

The permeate spacer (24) is optionally made from a natural fibre or a man-made fibre, e.g. polyester, polysulfone, polyester, nylon, teflon, polypropylene, polyphenylenesulfide, etc. The fibres are optionally resin coated, e.g. with a resin such as an epoxy or melamine resin.

Permeate spacers (24) having the required open space volume may be obtained commercially or they may be constructed from several macroporous sheets which each have an open space volume below that required by the present invention but which combined form a permeate spacers (24) having the required open space volume.

The desired aspect ratios may be made by cutting the membranes and permeate spacers such that they have the desired aspect ratio.

According to a second aspect of the present invention there is provided a gas separation module comprising a plurality of gas separation elements according to the first aspect of the present invention.

The total area of the permeate spacers (24) within the module is preferably at least 12 $m^2$, e.g. 12 to 25 $m^2$. As the open space of the permeate spacers (24) is at least 0.0004 $m^3/m^2$, the total open volume of permeate spacers (24) within the module is preferably at least twelve times that (for 12 $m^2$), more preferably twelve to twenty five times that (for 12 to 25 $m^2$), i.e. at least 0.0048 $m^3$ and preferably 0.0048 $m^3$ to 0.01 $m^3$.

The total area of the membrane sheets (18) within the module is preferably 75% to 125%, more preferably 90% to 110%, especially 95% to 105% and more especially 99% to 101%, of the total area of the permeate spacers (24) within the module.

Preferably the gas separation module is a spiral wound gas separation module. For example, the gas separation further comprises a perforated permeate collection tube (12) and the gas separation elements are wound around that tube (12) and are in gas communication therewith.

The function of the permeate collection tube (12), when present, is to collect the permeate gas which has passed through the membranes. Thus the gas separation elements are arranged such that the permeate can flow through the permeate collection tube perforations (14) and the retentate cannot flow through the permeate collection tube perforations (14).

The perforations (14) along the length of the permeate collection tube (12) allow gas flow from the exterior of the tube to the interior. Surrounding the permeate collection tube (12) and in gas communication therewith is a permeate spacer (24). The permeate spacer (24) typically transports the filtered permeate gas in a direction perpendicular to the axial length of the tube (12).

The permeate collection tube (12) is typically constructed of a rigid material, for example a metal (e.g. stainless steel) or a plastic.

Typically the module comprises a stack of the gas separation elements arranged such the feed spacer (16) and permeate spacers (24) alternate throughout the stack and the feed spacers (16) and permeate spacers (24) are separated by the membranes (18, or 18a, 18b).

Preferably the GSE further comprises a feed spacer (16). Preferred feed spacers (16) have a thickness of between 300 and 1,500 μm.

The feed spacer (16) and the permeate spacer (24) typically have a relatively large mesh size to allow the feed gas to travel axially along a membrane module (in the case of a spiral gas module). In most instances, the feed spacer (24)

will be present in the GSE and the module of the present invention, but it is possible to construct a GSE and modules without this component.

In general, a feed spacer (16) is formed of any inert material which maintains a space between the membrane(s) and is stable to the feed gas. Further, the feed spacer (16) allows the feed gas to be filtered to travel axially along the membrane module.

Preferred materials for the feed spacer (16) are open, channel forming grid materials, such as polymeric grid, or corrugated or mesh materials. Preferred among these are polypropylene or other polyolefin netting materials.

Typically the edges of adjacent membrane sheets (18a, 18b) which lie along the axial length of permeate collection tube are sealed so that gas flowing through feed spacer (16) is prevented from direct access to permeate collection tube (12). Alternatively, the membrane sheet (18) may be folded with the closed end being adjacent to the permeate collection tube (12) and with permeate spacer (24) located within the fold such that membrane surfaces (18) face one another.

The gas separation elements and feed spacer (16)(when present) may thus be spiral wound around a permeate collection tube (12) with the permeate spacer (24) in gas communication with the permeate collection tube (12). Referring to the series of layers of membrane sheet (18a), permeate spacer (24), second membrane sheet (18b) and feed spacer (16) as a gas separation element, typically a stack of gas separation elements are spiral wound about the permeate collection tube (12).

After the membrane module has been wound, the assembly may be held in a wound state through the use of restraining bands or outer wraps, or a combination thereof. A preferred method of restraining the assembly is by filament winding, in which a glass fibre filament dipped in an adhesive is wound around the assembly and cured. The modules can then be loaded into a housing or pressure vessel which is preferably operated at a slight pressure drop across the module as the gas being filtered flows through. In operation, the feed gas to be filtered is introduced at one end face of the membrane module, as illustrated in FIG. 3.

Figure 4:
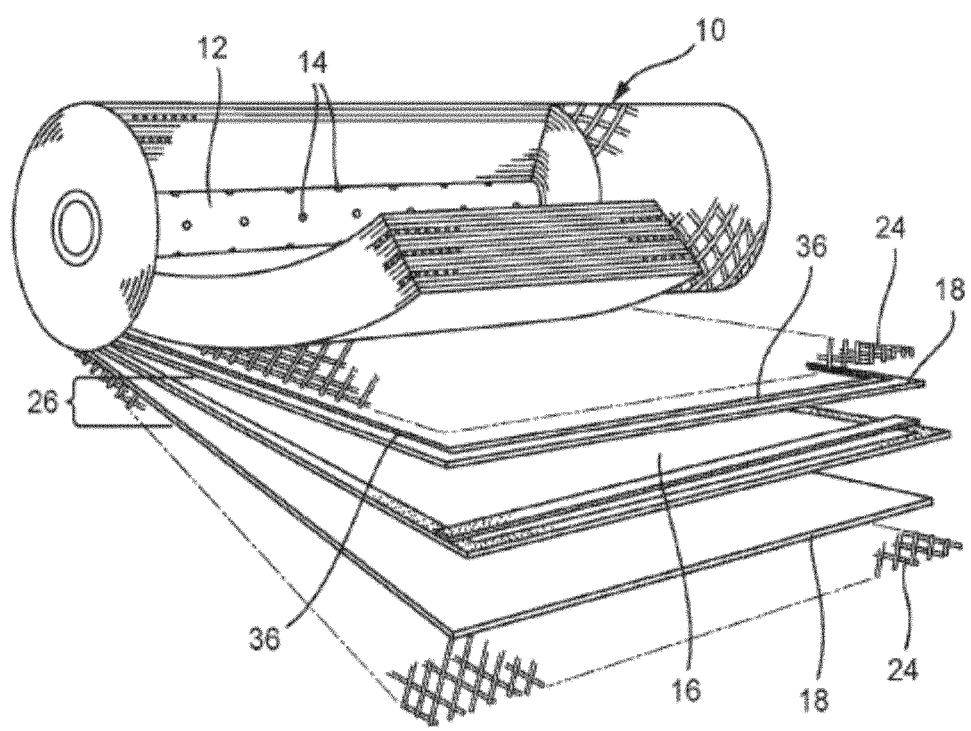
FIG. 4 is a partially exploded, perspective view of a gas separation module according to the present invention.

In a spiral wound gas separation module, the feed gas typically travels axially along membrane module through the feed spacer (16), as illustrated in FIG. 4. As the feed gas encounters the external surface of the membrane (18, or 18a, 18b), part of the feed gas (the permeate) passes through the membrane and into the permeate spacer (24). After the permeate gas has passed through the membrane (18, or 18a, 18b), it travels along the permeate spacer (24), eventually passing through perforations (14) and into the permeate collection tube (12). The permeate exits the membrane module through the central permeate collection tube (12) and the retentate travels axially through the module along the feed spacer (16). The effective area of the membranes in the module is preferably between 12 and 25 m².

As will be appreciated, in a spiral would gas separation module it is necessary to seal all of the edges of membrane envelopes (18, or 18a, 18b) to the permeate spacer, with the exception of the edges containing the permeate spacer (24) adjacent to the permeate collection tube (12), in order to prevent the feed gas from entering the permeate spacer (24) without first passing through the membrane. Thus it is necessary to prevent the feed gas from entering permeate spacer (24) without first being filtered as desired.

In the method of preparing the module according to the present invention, an adhesive may be applied to at least a part of the periphery of the membrane sheets, e.g. to the side edges and axial edges.

According to a third aspect of the present invention there is provided a process for separating and/or purifying a feed gas comprising at least a higher alkane and methane as gaseous components comprising passing the feed gas through a gas separation element according to the first aspect of the present invention or a module according to the second aspect of the present invention such that feed gas is separated into a permeate gas and a retentate gas, one of which is enriched in at least one of the said gaseous components and one of which is depleted in at least one of the said gaseous components.

According to a fourth aspect of the present invention there is provided the use of a gas separation element according to the first aspect of the present invention or a module according to second aspect of the present invention for separating gases and/or purifying a feed gas.

The invention will now be illustrated by the following, non-limiting examples.

Examples

The following test methods were used in the Examples:
(A) Patch Test Permeance and Selectivity The gas selectivity and permeance performance were measured using a feed gas having the composition described in Table 1 above which was passed through each gas membrane at a temperature of 40° C. at a gas feed pressure of 3,000 kPa using a gas permeation cell with a measurement diameter of 1.5 cm. Flow, pressure, and gas composition of each feed gas, permeate gas, and retentate gas was calculated according formulation described in "Calculation Methods for Multicomponent Gas Separation by Permeation" (Y. Shindo et al, Separation Science and Technology, Vol. 20, Iss. 5-6, 1985) with "countercurrent flow" mode.

The permeance ($Q_i$) of $CO_2$, $CH_4$ and $nC_4H_{10}$ was determined using the following equation:

$$Q_i = (\theta_{perm} \cdot X_{Perm,i})/(A \cdot (P_{Feed} \cdot X_{Feed,i} \cdot P_{perm} \cdot X_{Perm,i}))$$

wherein:
$Q_i$=Permeance of the relevant gas (i.e. is $CO_2$, $CH_4$ or $nC_4H_{10}$) ($m^3$(STP)/$m^2 \cdot kPa \cdot s$),
$\theta_{Perm}$=Permeate flow rate ($m^3$(STP)/s);
$X_{Perm,i}$=Volume fraction of the relevant gas in the permeate gas;
A=Membrane area ($m^2$);
$P_{Feed}$=Feed gas pressure (kPa);
$X_{Feed,i}$=Volume fraction of the relevant gas in the feed gas;
$P_{Perm}$=Permeate gas pressure (kPa); and
STP is standard temperature and pressure, which is defined here as 25.0° C. and 1 atmosphere pressure (101.325 kPa).

The GPU was then determined by 1 GPU=1×10$^{-6}$ cm³ (STP)/(s·cm²·cmHg).
In this test, a patch permeance of n-$C_4H_{10}$ above 800 GPU was deemed to be a 'fail' and a patch selectivity of below 800 GPU was deemed to be a 'pass'.

The membrane patch selectivity (n-$C_4H_{10}$/$CH_4$ selectivity; $\alpha$(n-$C_4H_{10}$/$CH_4$)) of each membrane under test for the gas mixture described in Table 1 was calculated from $Q_{(CH4)}$ and $Q_{(n-C4H10)}$ calculated as described in (A) above based on following equation:

$$\alpha(n\text{-}C_4H_{10}/CH_4) = Q_{(n\text{-}C4H10)}/Q_{(CH4)}$$

(B) Patch Robustness Test

The robustness of the each gas separation membrane was checked by evaluating its decline in selectivity after two weeks usage under the following conditions using gas feed composition $CO_2/CH_4/n$-$C_4H_{10}$/MeOH=13/85.5/1/0.5 at 40° C. at a pressure of 30 bar. In the patch test robustness, a decrease of 10% or more in at least one of $CO_2/CH_4$ selectivity, $CO_2/nCH_4$ selectivity or $CO_2$ permeance was deemed to be a 'fail' ("NOK") and a decrease of less than 10% was deemed to be a 'pass' ("OK").

(C) Module Permeance Test

The n-$C_4H_{10}$/$CH_4$ selectivity of spiral wound modules was measured at 30° C. using 30 bar 2,000 l/min air containing 5% of $CO_2/CH_4$/n-$C_4H_{10}$ (13/86/1) mixed gas in air in stage cut (=permeate flow amount/feed flow amount× 100%) below 30%.

The permeance of the membranes in the module was calculated by the patch test (A) described above. Modules having a n-$C_4H_{10}$ permeance of less than 70% were deemed to be a 'fail' and modules having a n-$C_4H_{10}$ permeance of 70% or more were deemed to be a 'pass'.

(D) Measurement of the Amount of Monovalent Metal Ions Present in the Porous Support In the following Examples, the amount of monovalent metal ions present in the porous support was determined as follows:

A sample of the PAN support under investigation of size 8.8 cm² was dissolved in concentrated (70%) nitric acid (5 cm³) by heating in a microwave (Anton Paar 3000 microwave) at 1200 W for 15 minutes. The dissolved sample was diluted with milli-Q (45 cm³) to give a clear solution (total volume 50 cm³). The content of monovalent metal ions in the clear solution was determined by multielemental inorganic analyses using a Perkin-Elmer 5300DV ICP-OES fitted with a concentric Type K nebulizer and a Cyclonic spray chamber. The concentration of monovalent metal ions in the clear solution was calculated as follows:

First the increase/decrease of the element signal (K) per wavelength was calculated:

$$K=(c_{add}-c)/c_{std}*100\%$$

K=correction factor increase/decrease element concentration;
$c_{add}$=concentration of the sample+standard addition, in mg/l;
c=concentration of the element analysed in the calibration line, in mg/l;
$c_{std}$=concentration of the added standard solution, in mg/l;

Then: $C_e=(c-c_{bl})*100/K*50/a*10$ $C_e$=concentration of the element;
$c_{bl}$=concentration of the element in the blank solution, in mg/l;
a=surface area of sample in cm².

Then the concentration of monovalent metal ions in the porous support in mg/m² was obtained by adding up all values CE for each element e.g. $Na^+$, $K^+$, $Li^+$, $Cs^+$ and $Li^+$.

Membranes

The following materials were used to prepare the Membranes described below.

PAN1 is a support having an average thickness of 170-180 μm comprising a PET nonwoven support (140-150 μm thick) having a porous polyacrylonitrile layer. PAN1 was obtained from Microdyn-Nadir GmbH, Germany, under the trade name UA100T and comprised 3.5 mg/m² of $Na^+$ (sodium ions).

PAN2 is a support having an average thickness of 180-190 μm comprising a PET nonwoven support (140-150 μm thick) having a porous polyacrylonitrile layer. PAN2 was obtained from GMT Membrantechnik GmbH, Germany under the trade name L14. PAN2 comprised 25 mg/m² monovalent ions (22 mg/m² of sodium ions and 3 mg/m² of potassium ions).

PAN3 was obtained by immersing PAN1 in 1 N NaOH solution at 60° C. for 3 hours and then rinsing with pure water and drying for 3 hours at 60° C. The resultant PAN3 comprised 3 mg/m² of sodium ions and 0.3 mg/m² potassium ions.

UV9300 is SilForce™ UV9300 from Momentive Performance Materials Holdings. This is a curable copolymer comprising at least 3 epoxy groups and linear polydimethyl siloxane chains. Furthermore, this copolymer cures rapidly when irradiated with UV light in the presence of a photo-initiator.

I0591 is 4-isopropyl-4'-methyldiphenyliodonium tetrakis (pentafluorophenyl) borate ($C_{40}H_{18}BF_{20}I$) from TCI (a photoinitiator).

Ti(OiPr)$_4$ is titanium (IV) isopropoxide from Dorf Ketal Chemicals.

n-Heptane is n-heptane from Brenntag Nederland BV.

FS1 is a net fabric as spacing material for membrane module which is sold under the name Naltex N01717_90PP-NAT by Delstar, a feed spacer having a thickness of 380 μm.

The following macroporous sheets ("MS") are used in the Examples to prepare permeate spacers:

| Abbreviation | Product name | Supplier | Description | V** Open space per m² (in %) | V Open Space per m² (in m³) | BW* (g/m2) | Thickness (μm) |
|---|---|---|---|---|---|---|---|
| MS1 | HW 2503 | Hornwood | PET fabric coated epoxy resin | 63 | 0.000191 | 158 | 305 |
| MS2 | GF 42369 | Guilford | PET fabric coated epoxy resin | 55 | 0.000168 | 190 | 305 |
| MS3 | GF 36168 | Guilford | PET fabric coated epoxy resin | 67 | 0.000203 | 142 | 305 |
| MS4 | GF 49064 | Guilford | PET fabric coated epoxy | 58 | 0.000146 | 150 | 254 |
| MS5 | 05TH100S | Hirose paper | PET nonwoven fabric | 37 | 0.00004306 | 100 | 115 |
| MS6 | N04607 | SWM | Poly(propylene) net | 82 | 0.00104 | 198 | 1168 |

*BW means base weight.
**Volume

Preparation of Porous Supports Comprising a Polysiloxane Discriminating Layer

Stage a) Preparation of a Partially Cured Polymer ("PCP Polymer")

A solution of a PCP Polymer was prepared by heating the components described in Table 2 together for 105 hours at 95° C. The resultant solution of PCP Polymer had a viscosity of about 64,300 mPas when measured at 25° C.

TABLE 2

Ingredients used to prepare PCP Polymer

| Ingredient | Amount (w/w %) |
|---|---|
| UV9300 | 50 |
| X-22-162C | 10 |
| n-heptane | 40 |

Stage b) Preparation of Radiation Curable Composition ("RCC1")

Portions of the solution of PCP Polymer obtained in stage a) above were cooled to 20° C., diluted with n-heptane and then filtered through a filter paper having an average pore size of 2.7 μm. The remaining ingredients indicated in Table 3 below were then added to make RCC1 as indicated in Table 3 below.

TABLE 3

| | Ingredient (w/w %) | RCC1 |
|---|---|---|
| Inert solvent | n-Heptane | 74.4 |
| | MEK | 5.0 |
| PCP Polymer | PCP Polymer | 20.0 |
| Adhesion promotor | Ti(OiPr)$_4$ | 0.5 |
| Photoinitiator | I0591 | 0.1 |

Stage c) Preparation of the Membranes

The membranes M1 to M8 described in Table 4 below were prepared by applying RCC1 obtained in stage b) above to the porous supports indicated in Table 4 by slot-die coating at a speed of 10 m/min. The RCC1 present on the porous supports was then cured using a Light Hammer LH10 from Fusion UV Systems fitted with a D-bulb by irradiating with an intensity of approximately 16.8 kW/m (70%). The resultant membrane sheets comprising a porous support and a discriminating layer were then evaluated in the Test (A) described above and the results are shown in Table 4 below.

TABLE 4

| Example | M1 | M2 | M3 | M4 | M5 | M6 | M7 | M8 |
|---|---|---|---|---|---|---|---|---|
| Porous support | PAN1 | PAN1 | PAN1 | PAN1 | PAN2 | PAN3 | PAN1 | PAN1 |
| Dry layer thickness of the discriminating layer (μm) | 1.2 | 1.8 | 2.4 | 3.0 | 2.4 | 2.4 | 0.6 | 4.0 |
| (A) Patch Test | 2.51 | 2.57 | 2.59 | 2.61 | 2.59 | 2.59 | 2.49 | 2.60 |
| Selectivity α(n-C$_4$H$_{10}$/CH$_4$) | OK | OK | OK | OK | OK | OK | OK | OK |
| Patch test (A) permeance | 700 | 490 | 400 | 300 | 400 | 400 | 840 | 150 |
| n-C$_4$H$_{10}$ gas permeance in GPU (800 or less is OK) | OK | OK | OK | OK | OK | OK | NOK | OK |

Preparation of Permeate Spacers

Permeate spacers PS1 to PS11 were prepared using the macroporous sheets described in Table 5 below. For permeate spacers comprising more than one macroporous sheet, three side edges of the macroporous sheets were glued together, leaving one edge free to feed permeate into permeate collection tube (16) which was fitted later.

TABLE 5

| | Permeate Spacer ("PS") | | | |
|---|---|---|---|---|
| PS | Macroporous Sheet(s) Used and their Order | PS thickness in total (μm) | PS open volume in total (m$^3$/m$^2$) | PS open ratio in total (%) |
| PS1 | MS1/MS1/MS1 | 915 | 0.00057 | 63% |
| PS2 | MS2/MS2/MS2 | 915 | 0.00050 | 55% |
| PS3 | MS3/MS3/MS3 | 915 | 0.00061 | 67% |
| PS4 | MS6 | 1168 | 0.00104 | 89% |
| PS5 | MS5/MS2/MS2/MS2/MS5 | 1145 | 0.00059 | 52% |
| PS6 | MS2/MS6/MS2 | 1778 | 0.00137 | 77% |
| PS7 | MS5/MS6/MS5 | 1398 | 0.00112 | 80% |
| PS8 (Comparative) | MS2 | 305 | 0.00017 | 55% |
| PS9 (Comparative) | MS2/MS2 | 610 | 0.00034 | 55% |
| PS10 | MS4/MS4/MS4 | 762 | 0.00044 | 58% |
| PS11 (Comparative) | MS5/MS5/MS5 | 345 | 0.00013 | 37% |

Preparation of Gas Separation Elements GSE1 to GSE17 and Modules Mod1 to Mod17

Gas separation elements GSE1 to GSE17 were prepared by gluing three sides of the membranes and permeate spacers together in the order indicated in Table 6 below. The ratio X/Y indicates the effective X width:Y length of the membrane for the modules after correction of glue lines.

TABLE 6

| Gas Separation Element | GSE | Module | n-C$_4$H$_{10}$ permeance ratio # | Rating * | Ratio X/Y |
|---|---|---|---|---|---|
| GSE1 | M3/PS1/M3 | Mod1 | 78 | Good | 2.1 |
| GSE2 | M3/PS2/M3 | Mod2 | 78 | Good | 2.1 |
| GSE3 | M3/PS3/M3 | Mod3 | 78 | Good | 2.1 |
| GSE4 | M3/PS4/M3 | Mod4 | 71 | Good | 2.1 |
| GSE5 | M3/PS5/M3 | Mod5 | 82 | Good | 2.1 |
| GSE6 | M3/PS6/M3 | Mod6 | 79 | Good | 2.1 |
| GSE7 | M3/PS7/M3 | Mod7 | 80 | Good | 2.1 |
| GSE8 | M4/PS2/M4 | Mod8 | 80 | Good | 2.1 |
| GSE9 (Comparative) | M3/PS8/M3 | Mod9 (Comparative) | 45 | Unacceptable | 2.1 |

TABLE 6-continued

| Gas Separation Element | GSE | Module | n-$C_4H_{10}$ permeance ratio # | Rating * | Ratio X/Y |
|---|---|---|---|---|---|
| E10 (Comparative) | M3/PS9/M3 | Mod10 (Comparative) | 53 | Unacceptable | 2.1 |
| GSE11 | M3/PS10/M3 | Mod11 | 65 | Good | 2.1 |
| GSE12 (Comparative) | M3/PS11/M3 | Mod12 (Comparative) | 44 | Unacceptable | 2.1 |
| GSE13 | M1/PS2/M1 | Mod13 | 58 | Acceptable | 2.1 |
| GSE14 | M2/PS2/M2 | Mod14 | 55 | Acceptable | 2.1 |
| GSE15 | M3/PS2/M3 | Mod15 | 45 | Unacceptable | 1.1 |
| GSE16 | M3/PS2/M3 | Mod16 | 72 | Good | 1.7 |
| GSE17 | M8/PS2/M8 | Mod17 | 79 | Good | 2.1 |

The n-$C_4H_{10}$ permeance ratio is the (Patch Test (A) permeance for porous support (e.g. M3 in Mod 1))/(Module Test (C) permeance (e.g. Mod 1 for the first row of results in Table 6)).
* An-$C_4H_{10}$ permeance ratio of >60% was rated as good.
An-$C_4H_{10}$ permeance in the range 55 to 60% was rated as acceptable.
An-$C_4H_{10}$ permeance ratio below 55% was rated as unacceptable.

Preparation of Modules

For each module, one type of GSE indicated in Table 6 was glued to a perforated collection tube (12) of external diameter 50 mm (internal diameter 47 mm) with perforations (14) of 4 mm diameter through the tube (12) wall (to give an aperture ratio of 15-20%). A feed spacer (FS1) was included between each of the GSEs shown in Table 6 and the next (to allow the influx of feed gases to the side of the membranes opposite to the permeate spacers). In total 16 m² of membrane was included in each module. The effective X-length of the gas separation elements was 840 mm and effective Y-width was 400 mm for almost all modules except for module Mod15 and module Mod16 wherein the effective Y-width for the GSE were respectively 750 mm and 500 mm. The non-glued edges were fixed to the perforated collection tube (12) such that gas which permeated through the membranes (18) could flow through the permeate spacer (24), through the perforations (14) and into the perforated collection tube (12), but gas which did not permeate through the membrane (18) could not enter the perforated collection tube (12). For each module the gas separation elements (which each included a feed spacers (16)) were wound around a perforated collection tube (12). The resultant structure was encased in fibreglass and anti-telescoping devices were glued to each corner cylinder side to give gas separation modules. The modules were then cased in a steel housing and tested for gas permeance by the above described method (B), providing the results shown in Table 6 above.

The invention claimed is:

1. A gas separation element comprising a membrane sheet and a permeate spacer, wherein the membrane sheet comprises a porous support and a discriminating layer wherein
   (a) the permeate spacer has an open space volume of 0.00046 m³/m² to 0.0020 m³/m²; and
   (b) the membrane sheet has an aspect ratio of at least 1.5.

2. The gas separation element according to claim 1 wherein the membrane sheet has a n-$C_4H_{10}$ gas permeance of 30 to 800 GPU.

3. The gas separation element according to claim 1 wherein the discriminating layer has an average thickness of at least 0.7 µm.

4. The gas separation element according to claim 1 wherein the porous support comprises a porous PAN support.

5. The gas separation element according to claim 1 wherein the permeate spacer comprises one or more macroporous sheets.

6. The gas separation element according to claim 5 wherein the permeate spacer further comprises one or more protective sheets which shield at least a part of the membrane from contact with the one or more macroporous sheets.

7. The gas separation element according to claim 1 wherein the permeate spacer has an average thickness of at least 900 µm.

8. The gas separation element according to claim 1 which further comprises a feed spacer.

9. The gas separation element according to claim 8 wherein the feed spacer has an average thickness between 300 and 1500 µm.

10. The gas separation element according to claim 8 wherein the membrane sheet is folded around the permeate spacer to form a membrane envelope such that gas may pass through the feed spacer and then permeate through the membrane and into the permeate spacer.

11. The gas separation element according to claim 1 wherein the discriminating layer has an average thickness of at least 1.2 µm.

12. The gas separation element according to claim 1 wherein the discriminating layer comprises a polysiloxane.

13. A spiral wound gas separation module comprising a plurality of gas separation elements according to claim 1.

14. The gas separation module according to claim 13 wherein the total area of the permeate spacers within the module is at least 12 m².

15. The gas separation module according to claim 13 wherein the total area of the permeate spacers within the module is 12 to 25 m².

16. The gas separation module according to claim 13 wherein the total area of the membrane sheets within the module is 75% to 125% of the total area of the permeate spacers within the module.

17. The gas separation module according to claim 13 comprising a stack of the gas separation elements arranged such the permeate spacers and feed spacers alternate throughout the stack and the permeate spacers and feed spacers are separated by the membranes.

18. The gas separation module according to claim 13 wherein the gas separation elements are spirally wound around a permeate collection tube with an open end of the permeate spacer located adjacent to the tube and in gas communication therewith.

19. A process for separating and/or purifying a feed gas comprising at least a higher alkane and methane as gaseous components comprising passing the feed gas through a gas separation element according to claim 1 or a gas separation module comprising a plurality of gas separation elements according to claim 1 such that feed gas is separated into a permeate gas and a retentate gas, one of which is enriched in at least one of the said gaseous components and one of which is depleted in at least one of the said gaseous components.

20. The gas separation element according to claim 1 wherein the discriminating layer comprises a polysiloxane and wherein the membrane sheet has a n-$C_4H_{10}$ gas permeance of 150 to 700 GPU.

* * * * *